United States Patent [19]

Boileau et al.

[11] 4,365,094
[45] Dec. 21, 1982

[54] PROCESS FOR THE SYNTHESIS OF TERTIARY PHOSPHINE OXIDES, AND NEW TERTIARY PHOSPHINE OXIDES

[75] Inventors: Sylvie L. Boileau; Thanh-Dung N'Guyen, both of Paris; Jean-Claude C. Gautier, Ablon sur Seine, all of France

[73] Assignee: Societe Nationale des Poudres et Explosifs, Paris, France

[21] Appl. No.: 213,212

[22] Filed: Dec. 5, 1980

[30] Foreign Application Priority Data

Dec. 28, 1979 [FR] France .................................. 79 31917

[51] Int. Cl.³ ................................................ C07F 9/53
[52] U.S. Cl. ........................................................ 568/14
[58] Field of Search ..................................... 568/11, 14

[56] References Cited

U.S. PATENT DOCUMENTS

| | | | |
|---|---|---|---|
| 2,900,416 | 8/1959 | Stewart et al. | 568/8 |
| 3,304,330 | 2/1967 | Yoke et al. | 568/14 |
| 3,316,293 | 4/1967 | Carr et al. | 568/14 |
| 3,382,173 | 5/1968 | Lorn et al. | 568/8 |
| 3,389,183 | 6/1968 | Hays | 568/8 |
| 3,657,352 | 4/1972 | Kleiner | 568/14 |

*Primary Examiner*—Helen M. S. Sneed
*Attorney, Agent, or Firm*—Bucknam and Archer

[57] ABSTRACT

The invention relates to the synthesis of tertiary phosphine oxides and also to certain tertiary phosphine oxides.

According to the invention, an organic phase containing a halogenomethyl derivative, a secondary phosphine oxide and a phase transfer catalyst in an organic medium is reacted with an aqueous phase containing an inorganic base. The halogenomethyl derivative can be a micromolecule or a macromolecule.

The tertiary phosphine oxides are substances which are useful, in particular, in fireproofing, in hydrometallurgy and in the field of plant health.

12 Claims, No Drawings

PROCESS FOR THE SYNTHESIS OF TERTIARY PHOSPHINE OXIDES, AND NEW TERTIARY PHOSPHINE OXIDES

The invention relates to the synthesis of tertiary phosphine oxides and also to certain tertiary phosphine oxides by way of new products.

In the past, very diverse processes have been proposed for the synthesis of tertiary phosphine oxides. Some of these processes use a Grignard reagent together either with phosphorus oxychloride, as in French Pat. No. 2,159,716 of it, or with a mixture of phosphorus trichloride and oxygen, as in French Pat. No. 1,399,743, or with a phosphonyl chloride, as in U.S. Pat. No. 3,258,492, or also with a dialkyl phosphite and an organic halide, as in French Pat. No. 2,346,361.

Other processes use a technique involving thermal decomposition, for example of the product resulting from the addition of a dialkyl phosphite oxide onto an α-olefine, as in German Pat. No. 1,912,708, of a quaternary phosphonium halide, as in French Pat. No. 2,316,244, of a hydroxylic quaternary phosphonium halide, as in U.S. Pat. No. 3,997,611, or also of a tertiary hydroxymethylphosphine, as in U.S. Pat. No. 4,020,110.

Further processes involve phosphorus and an alkyl iodide in the presence of iodine, as in French Pat. No. 2,352,824.

These known processes are characterised by being somewhat expensive, by the existence of secondary reactions which are difficult to control, and by the use of drastic operating conditions, especially as regards the temperature and the solvents, which must be dry. Furthermore, they do not make it possible easily to obtain phosphine oxides of the type RRR'PO, in particular those of this type in which R' is a polymeric chain of high molecular weight.

The Applicant Company has now found a process for the synthesis of phosphine oxides using relatively mild and simple conditions, which does not give rise to secondary reactions and does not require dry solvents.

The process of synthesis according to the invention is a process for the synthesis of tertiary phosphine oxides from a dialkylphosphine oxide, characterised in that a secondary phosphine oxide is reacted with a halogenomethyl derivative in an organic medium, in the presence of a phase transfer catalyst and whilst stirring.

According to a preferred modified embodiment of the process according to the invention, the secondary phosphine oxides used have the general formula:

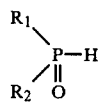

in which $R_1$ and $R_2$ are identical or different and are a linear or branched alkyl group containing from 1 to 18 carbon atoms, preferably from 1 to 12 carbon atoms, or also a phenyl group. Particularly suitable phosphine oxides which may be mentioned are diethyl-, di-n-propyl-, di-n-butyl-, di-n-hexyl-, di-(2-ethylhexyl)-, di-n-octyl-, di-n-dodecyl-, methyloctyl-, ethylbutyl-, ethylheptyl-, ethylnonyl-, propyloctyl- and diphenyl-phosphine oxides and the like.

Halogenomethyl derivatives which fall well within the scope of the invention are, in particular, those of the general formula $XCH_2R$, in which: X is a chlorine or bromine atom and R is a group $—CH=CHY$, in which Y is a hydrogen atom, a phenyl group or a group $—CH_2X$, in which X has one of the meanings indicated above, or alternatively R is a group

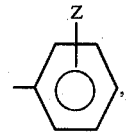

in which Z is a hydrogen atom, a $C_1$ to $C_4$ alkyl group, a vinyl group, a halogen atom, a group $—CH_2X$ or a group

X having one of the meanings indicated above, or alternatively R is an alkyl chain containing from 1 to 12 carbon atoms, which is optionally substituted by at least one nitrile or epoxy group, or alternatively R is a phenyl group forming part of a random copolymer chain containing styrene and a p-halogenomethylstyrene, which has a molecular weight of between 500 and 1,000,000 and comprises x and y units

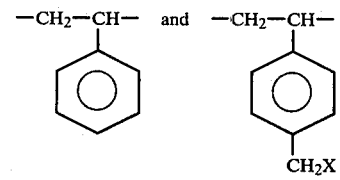

respectively, x and y being integers such that the ratio x:y is between 100:1 and 0:1, or alternatively R is a phenyl group forming part of a random copolymer chain containing styrene and a halogenomethylstyrene, which is partially crosslinked, is referred to as a Merrifield resin, has a molecular weight of between 1,000 and 1,000,000 and comprises x, y and z units

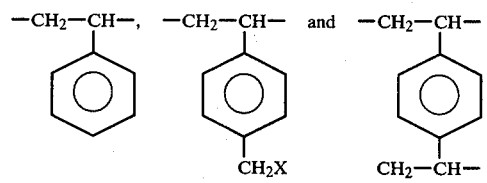

respectively, x, y and z being integers such that the ratio x:y is between 100:1 and 0:1 and such that the ratio z:y is between 1:25 and 1:5.

It is preferred to use a halogenomethyl derivative which, in isolation, is not sensitive to strong inorganic bases, that is to say a derivative which, when brought by itself into the presence of a base of this type, does not react or degrade rapidly.

The organic solvent used within the scope of the invention must be a common solvent for the dialkylphosphine oxide and for the halogenomethyl derivative, must not be miscible with the alkaline aqueous phase and must preferably be slightly polar or non-polar, that is to say it must have a dielectric constant of less than 8 at 20° C. It is immaterial whether the solvent is protic or aprotic. Suitable solvents which may be mentioned are aromatic solvents, such as benzene, toluene and xylenes, and aliphatic solvents. Mixtures of solvents are also suitable. It is also possible to carry out the reaction in bulk, without a solvent.

The aqueous alkaline phase must contain an amount of inorganic alkaline base which is at least equal to the stoichiometric amount for the reaction, which consists overall of a condensation with the release of one molecule of hydrohalic acid per molecule of halogenomethyl derivative.

In practice, the aqueous alkaline phase must contain from 30% to 60% by weight of an inorganic base. The latter is preferably sodium hydroxide or potassium hydroxide, although other bases, such as lime, can be used.

The ratio of the volume of aqueous phase to the volume of organic phase is not highly critical, but in practice is between the extreme values of 5:1 and 1:10. It is desirable to stir the reaction medium so as to promote contact between the organic and aqueous phases. Vigorous stirring has the effect of considerably accelerating the reaction rate.

The reaction is not sensitive to pressure, wherefore it is conveniently carried out under atmospheric pressure. On the other hand, the temperature is a critical factor because, below 0° C., the reaction is extremely slow, or even non-existent, and above 90° C., the reaction is in practice very difficult to carry out successfully and is accompanied by degradation of the products formed. A temperature between 40° and 70° C. generally gives the best results. The reaction is advantageously carried out under an inert atmosphere consisting of argon or nitrogen. If it is desired to obtain a high yield, relative to the halogen derivative (or relative to the phosphine oxide), it is important to employ an amount of secondary phosphine oxide (or, respectively, of halogenomethyl derivative) which is at least equal to the stoichiometric amount, relative to the halogenomethyl derivative (or, respectively, relative to the phosphine oxide).

However, although the molar ratio P/Cl is advantageously greater than 1, a value of more than 1.5 is to no advantage, except in the case where the halogenomethyl derivative is a resin, in particular of the random copolymer type indicated above.

As regards the concentration of the reactants in the organic phase, it is in practice between 1 and 20% by weight, relative to the solvent, and between 0.1 and 10% if the reactant is a polymer. However, it is also possible to carry out the reaction in bulk.

The reaction time varies from a few tens of minutes to a few tens of hours, depending on the temperature used and depending in particular on the nature of the phase transfer catalyst used.

The phase transfer catalysts of which the use is absolutely essential within the scope of the present invention are those conventionally used in reactions involving phase transfer catalysis. Two groups of these catalysts can be distinguished.

The first group comprises ionic phase transfer catalysts, which include the quaternary ammonium, phosphonium or arsonium salts of the general formula:

$$A_1A_2A_3A_4Y^+.X^-$$

in which Y=N, P or As, $A_1$, $A_2$, $A_3$ and $A_4$ are identical or different and are preferably $C_1$ to $C_8$ alkyl groups, benzyl groups or polymer chains, and $X^-$ is an anion.

Preferably, $X^-$ is a halide, carboxylate, hydrogen sulphate or hydroxide anion. The second group comprises non-ionic complexing agents, which include polyethylene oxides, crown ethers and cryptands. Crown ethers are macrocyclic polyethers in which certain oxygen atoms can be substituted by sulphur atoms, while cryptands are macropolyheterocyclic compounds comprising polyether heterocyclic rings in which certain oxygen atoms can be replaced by sulphur, the said heterocyclic rings being bridged by nitrogen atoms. These complexing agents have the property of forming, with alkali metal and alkaline earth metal cations, complexes possessing an extremely high stability constant. They are extensively described in Jean-Marie LEHN, Design of Organic Complexing Agents—Strategies towards Properties, Structure and Bonding, Volume 16, Springer Verlag (1973), in an article by E. VOGTLE and E. WEBER, published in Kontakte, Volume 1, pages 11 to 31 (1977), and entitled Neutrale Organische Komplexliganden und ihre Alkalikomplexe—Kronenäther, Cryptanden, Podanden (Neutral Organic Complexing Ligands and their Alkali Metal Complexes—Crown Ethers, Cryptands, Podands), and also in French Pat. Nos. 2,201,304 and 2,398,079. The crown ethers and the cryptands can be used either in the form of free molecules or in a form which is fixed to a polymer. However, this latter solution to the problem is not recommended when the halogenomethyl derivative is itself a polymer. Amongst the crown ethers and the cryptands, it is preferred to use those which form, with the cation of the alkali metal base employed, complexes having a particularly high stability constant. The complexing agents of this type which are particularly preferred are well known to those skilled in the art. Reference may advantageously be made to the article by C. Kappenstein published in Bulletin de al Société Chimique de France, No. 1–2, pages 89 to 109 (1974). Thus, if sodium hydroxide is employed in the aqueous phase, it is advantageous to use 1,4,7,10,13,16-hexaoxacyclooctadeca-2,11-diene, or dibenzo-18-crown-6 according to the nomenclature of Pedersen, J.Amer.Chem.Soc., 1967, 89, page 7,017, cyclohexyl-15-crown-5, 18-crown-6 and dicyclohexyl-18-crown-6, or alternatively the cryptands 222 and 221, designated according to the nomenclature of J. M. Lehn (op. cit.) and Kappenstein (op. cit.). Potassium hydroxide is advantageously used in association with 18-crown-6, dicyclohexyl-18-crown-6 and cyclohexyl-18-crown-6, and 222, 221 and 322. Finally, if lime is used, the conditions are substantially the same as in the case of Na+ and it is advantageous to employ 18-crown-6 or dicyclohexyl-18-crown-6, or alternatively 222 or 221, or alternatively the cryptands, fixed to a polymer, marketed by the Société MERCK under the names Kryptofix 222 B polymer or Kryptofix 221 B polymer, in which the polymer residue is derived from a Merrifield resin. Many other crown ethers or cryptands are perfectly suitable within the scope of the invention, but these are compounds which give the impression of being laboratory curiosities.

Although the macroheterocyclic complexing agents generally prove wholly satisfactory within the scope of the invention, the quaternary ammonium salts, which are at least as effective and much less expensive, are preferred thereto as a general rule. As regards the phosphonium or arsonium salts, their activity is generally identical to that of the corresponding quaternary ammonium salts, but, on the other hand, they are substantially more expensive.

The amount of catalyst to be used is of the order of at least 1 mol %, relative to the halogen contained in the halogenomethyl derivative. Advantageously, a proportion of about 5 mol % will in fact be used. An excess of catalyst of more than 10 mol % appears to be neither disadvantageous nor advantageous.

It must be noted that it is conventionally acknowledged in the field of phase transfer catalysis (Makosza et al., J. Org. Chem. 43, 4,682 (1978)) that sodium carbonate or potassium carbonate, associated with a phase transfer catalyst such as dicyclohexyl-18-crown-6, constitute excellent bases for this kind of reaction. It has been shown that, within the scope of the invention, these associations have on the whole a moderate activity, because they only result in moderate to low yields, in particular in the case of polymerised halogenomethyl derivatives. This surprising phenomenon has not been explained. Once the reaction is complete, the reaction medium is cooled and the organic phase is separated from the aqueous phase and then treated. This treatment can consist in washing with a dilute acid solution, if appropriate after dilution of the said organic phase with an organic solvent. In the case where the halogenomethyl derivative is a polymer, this treatment can also consist in first precipitating the mixture in methanol and in purifying the precipitate by successive dissolutions in chloroform and reprecipitations in methanol.

The yields obtained by the process according to the invention are generally extremely high, in particular when starting from halogenomethyl micromolecules, in which case the said yields are regularly of the order of 95 to 100%. In the case of resins, it is possible easily to modify the degree of substitution between 10 and 90% by varying the solvent used and especially the catalyst used, and also by varying the reaction time and the temperature.

The invention also relates to the new industrial products of the general formula:

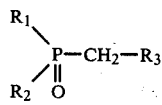

in which $R_1$ and $R_2$ are identical or different and are a linear or branched alkyl group containing from 1 to 18 carbon atoms, preferably from 1 to 12 carbon atoms, or a phenyl group, and $R_3$ is chosen from the group comprising:

(a) a group $-CH=CH_2R_4$, in which $R_4$ is a hydrogen atom or a group

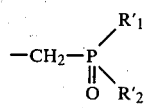

$R'_1$ and $R'_2$ having the same meanings as $R_1$ and $R_2$, (b) a group

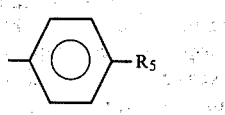

in which $R_5$ is a group

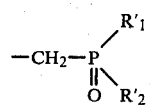

or a group

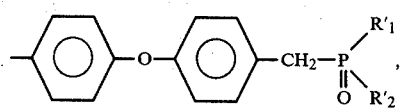

(c) a phenyl group forming part of one of the units

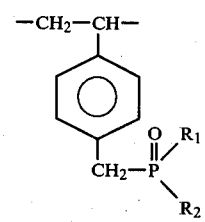

of a random copolymer derived from a random copolymer of styrene and a p-halogenomethylstyrene, which has a molecular weight of between 550 and 1,100,000 and comprises x and y units

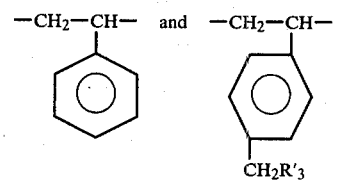

respectively, x and y being integers such that the ratio x:y is between 100:1 and 0:1, 20 to 90% by number of the $R_3$ groups being a group

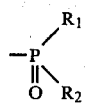

and 10 to 80% being a chlorine or bromine atom, or (d) a phenyl group forming part of one of the units

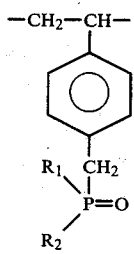

of a random copolymer derived from a random copolymer of styrene and a p-halogenomethylstyrene, which is partially crosslinked, is referred to as a Merrifield resin, has a molecular weight of between 1,100 and 1,100,000 and comprises x, y and z units

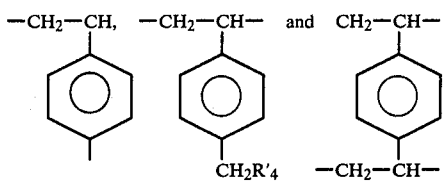

respectively, x, y and z being integers such that the ratio x:y is between 100:1 and 0:1 and such that the ratio z:y is between 1:25 and 1:5, 20 to 95% by number of the $R'_4$ groups being groups

and 5 to 80% being chlorine or bromine atoms.

Particularly preferred products according to the invention are those which carry n-octyl radicals as $R_1$ and $R_2$.

The products according to the invention are applied, in particular, in plant health formulations, as fireproofing compounds and as extraction agents.

The invention is further illustrated by the following non-limiting examples, which are carried out under a nitrogen atmosphere unless expressly stated to the contrary.

The secondary phosphine oxides used in the examples were obtained by reacting diethyl phosphite with an alkylmagnesium chloride or phenylmagnesium chloride, in THF under reflux, in accordance with the method described by R. H. Williams and L. A. Hamilton, Journal of the American Chemical Society, 74, 5,418 (1952) and 77, 3,411 (1955).

EXAMPLE 1

A heterogeneous mixture composed of dioctylphosphine oxide (DOPO) (5.3 mM), 15 ml of toluene, benzyl chloride (7.9 mM), 5 ml of a 50% strength by weight aqueous solution of sodium hydroxide and a phase transfer catalyst, namely tetrabutylammonium hydrogen sulphate (hereafter referred to as TBAH), in an amount of 0.16 mM, was stirred.

This mixture was stirred for 3 hours at 65° C. under a nitrogen atmosphere. The organic phase was subsequently diluted with 25 ml of methylene chloride and then separated from the aqueous phase was washed successively with an aqueous solution of hydrochloric acid (30 ml of 0.01 N acid) and then with water. The organic phase was dried over $MgSO_4$, after which the solvents were driven off and benzyldioctylphosphine oxide was collected with a yield of 100%, relative to the starting DOPO. This product was recrystallised from a mixture of acetone/water, after which a white powder was obtained, which melts at 59°–60° C. and possesses the following spectra:

Infra-red: band at 1,165 $cm^{-1}$ (P=O); band at 1,600 $cm^{-1}$ (phenyl).

NMR: singlet (5H, $C_6H_5$) at 7.28 ppm; doublet (2H, $CH_2$) at 3.08 ppm; multiplet (34H, $2C_8H_{17}$) between 1.53 and 0.85 ppm.

The elementary analysis confirms the compound $C_{23}H_{41}OP$:

|  | C | H | O | P |
| --- | --- | --- | --- | --- |
| % calculated | 75.83 | 11.26 | 4.40 | 8.51 |
| % found | 75.7 | 11.2 | 4.4 | 8.7 |

EXAMPLE 2

The previous experiment was repeated in every respect, except that the stirring lasted 4 hours and the TBAH was replaced by the cryptand 222. A yield of 100% of a product identical in every respect to the previous product was again obtained.

EXAMPLE 3

By way of comparison, the same experiment as described above was carried out using neither TBAH nor 222.

The yield of the reaction is zero, even at 80° C. after 6 hours.

EXAMPLES 4 TO 6

The influence of the concentration of the inorganic base in aqueous phase was studied.

To do this, the reaction was carried out by stirring a mixture, at 65° C., of 8.70 mM of benzyl chloride, 5.30 mM of DOPO, 0.164 mM of TBAH, 5 ml of 50% strength by weight aqueous sodium hydroxide solution, 5.11 mM of undecane and 15 ml of toluene.

The variation in the concentration of the benzyl chloride remaining in the organic phase was measured as a function of time.

The results are reported in Table 1 below:

| Time (minutes) | Benzyl chloride concentration (in mM) | Degree of conversion (in %) |
| --- | --- | --- |
| 0 | 9.128 | 0 |
| 10 | 8.036 | 20.6 |
| 20 | 6.677 | 46.3 |
| 30 | 5.960 | 59.8 |
| 60 | 5.593 | 66.8 |
| 90 | 5.147 | 74.6 |
| 120 | 4.876 | 80.3 |

It is seen that the yield is already excellent after two hours. The same procedure was then followed, but with 30% strength sodium hydroxide solution. To do this, a mixture, kept at 65° C., of 8.70 mM of benzyl chloride, 5.28 mM of DOPO, 0.160 mM of TBAH, 5 ml of 30% strength by weight aqueous NaOH solution, 5.13 mM of undecane and 15 ml of toluene was stirred.

The results obtained are entered in Table 2 below:

| Time (minutes) | Benzyl chloride concentration (in mM) | Degree of conversion (in %) |
| --- | --- | --- |
| 0 | 8.630 | 0 |
| 10 | 8.351 | 5.3 |
| 30 | 7.983 | 12.3 |
| 60 | 7.490 | 21.6 |
| 120 | 6.762 | 35.4 |
| 180 | 5.910 | 51.5 |

It is seen that, with 30% strength NaOH solution, the yield only starts to reach a suitable value after 3 hours.

Finally, an operation comparable to the previous two operations was carried out using 10% strength by weight sodium hydroxide solution. The conversion is zero after 3 hours.

In fact, it is only possible to obtain a substantial conversion with an inorganic base present in an amount of more than 20% by weight in the aqueous phase.

EXAMPLES 7 TO 9

The influence of the temperature in the process according to the invention was studied. Table 1 above summarises the results obtained at 65° C.

In addition, a mixture, at 50° C., consisting of 8.70 mM of benzyl chloride, 5.310 mmols of DOPO, 5.132 mM of undecane, 0.162 mM of TBAH, 5 ml of 50% strength aqueous sodium hydroxide solution and 15 ml of toluene was stirred.

The results recorded with time are entered in Table 3 below:

| Time (minutes) | Benzyl chloride concentration (in mM) | Degree of conversion (in %) |
| --- | --- | --- |
| 0 | 9.085 | 0 |
| 10 | 8.103 | 18.5 |
| 20 | 7.175 | 36.0 |
| 30 | 6.528 | 48.1 |
| 60 | 4.506 | 86.2 |

It is seen that, at 50° C., the process gives results which are at least as good as those at 65° C. for dioctylbenzylphosphine oxide.

The reaction was also carried out at 25° C., using a mixture of 5.388 mM of benzyl chloride, 5.293 mM of DOPO, 5.120 mM of undecane, 0.160 mM of TBAH, 5 ml of 50% strength aqueous sodium hydroxide solution and 30 ml of toluene.

It was found that the conversion was only 21.3% after one hour. The optimum temperature range seems to be situated between about 40° and 70° C.

EXAMPLES 10 TO 13

Various phase transfer catalysts of the ionic type were tested.

Thus, a mixture of 8.699 mM of benzyl chloride, 5.295 mM of DOPO, 5.129 mM of undecane, 5 ml of 50% strength aqueous NaOH solution, 15 ml of toluene and 0.167 mM of tetraethylammonium bromide, $Et_4N^+Br^-$, was stirred at 65° C.

The course of the reaction as a function of time is reported in Table 5 below:

| Time (minutes) | Benzyl chloride concentration (in mM) | Degree of conversion (in %) |
| --- | --- | --- |
| 0 | 8.711 | 0 |
| 15 | 8.502 | 4 |
| 30 | 8.360 | 7 |
| 60 | 7.803 | 17 |
| 90 | 7.616 | 21 |
| 120 | 7.081 | 31 |
| 150 | 6.429 | 43 |

The reaction is slower than with TBAH.

The reaction was carried out under the same conditions as in the previous experiment, but a different catalyst, namely tetraphenylphosphonium chloride, was used.

After one hour, the degree of conversion is 17%.

The same experiment was repeated, this time using tetraphenylarsonium chloride. Like the previous catalyst, this catalyst is sensitive at a temperature of 65° C., at which the degree of conversion is 10% after three hours.

Finally, an experiment was carried out with tetraheptylammonium chloride. To do this, a mixture of 5.436 mM of benzyl chloride, 5.297 mM of DOPO, 5.153 mM of undecane, 5 ml of 50% strength aqueous NaOH solution, 15 ml of toluene and 0.163 mM of $(C_7H_{15})_4NCl$ was stirred at 65° C.

The results collected as a function of time are entered in Table 6 below:

| Time (minutes) | Benzyl chloride concentration (in mM) | Degree of conversion (in %) |
| --- | --- | --- |
| 0 | 4.939 | 0 |
| 30 | 3.150 | 36.2 |
| 60 | 1.932 | 60.9 |
| 120 | 1.470 | 70.2 |
| 180 | 1.260 | 74.5 |

EXAMPLE 14

This time, potassium hydroxide was used as the inorganic base.

A mixture of 7.9 mM of benzyl chloride, 5.3 mM of DOPO, 0.16 mM of TBAH, 5 ml of 50% strength by weight aqueous KOH solution and 15 ml of toluene was stirred for 3 hours at 65° C.

A yield of 100% was recorded.

EXAMPLES 15 TO 17

The reaction was carried out under the same conditions as in Example 1, the TBAH, which is an ionic phase transfer catalyst, being replaced by various phase transfer catalysts of the type comprising macroheterocyclic complexing agents.

Thus, the cryptands 222 (or 4,7,13,16,21,24-hexaoxa-1,10-diazabicyclo[8,8,8]hexacosane) and 222 BB (or 5,6-14,15-dibenzo-4,7,13,16,21,24-hexaoxa-1,10-diazabicyclo[8,8,8]hexacosane) and the crown ether DCHE (or dicyclohexyl-18-crown-6) were used.

The results obtained as a function of time are reported in Table 7 below:

| Degree of conversion | Catalyst | | |
| --- | --- | --- | --- |
| | 222 | 222 BB | DCHE |
| after 0.5 hour | 20% | 13% | — |
| after 1 hour | 39% | 24% | 11% |
| after 1.5 hours | 53% | 34% | 19% |
| after 2 hours | 65% | 45% | 20% |
| after 2.5 hours | 79% | 47% | 28% |
| after 3 hours | — | 48% | 34% |
| after 3.5 hours | 93% | 57% | 42% |
| after 4 hours | 100% | 61% | 44% |
| after 4.5 hours | — | — | 53% |

It is seen that 222 BB and DCHE give satisfactory results, but that only 222 competes with tetrabutylammonium hydrogen sulphate.

EXAMAPLE 18

The DOPO in Example 1 was replaced by diphenylphosphine oxide. The reaction was carried out at 65° C. and a mixture of 9.98 mM of diphenylphosphine oxide, 14.97 mM of benzyl chloride, 10 ml of 50% strength aqueous sodium hydroxide solution, 0.5 mM of TBAH and 20 ml of toluene was stirred for 3 hours.

The crude product was treated as in Example 1, but recrystallised from toluene. This yielded 1.635 g of a product in the form of white crystals, which melts at 189°–190° C. and was identified by its spectra as indeed being diphenylbenzylphosphine oxide. The yield was 56% (oxide).

Infra-red spectrum: bands at 1,600 and 1,490 cm$^{-1}$ (phenyl); P=O band at 1,175 cm$^{-1}$.

NMR spectrum: 10 H at 7.55 ppm (2 phenyl groups); 5 H at 7.22 ppm (1 benzyl group); 2 H at 3.80 and 3.60 ppm (methylene).

EXAMPLE 19

The procedure of Example 1 was repeated using 5.47 mM of octyl chloride, 3.65 mM of DOPO, 5 ml of 50% strength aqueous sodium hydroxide solution, 0.18 mM of TBAH and 10 ml of toluene.

The reaction is stopped after 6 hours. The excess DOPO was removed by washing 3 times with acetone at −15° C.

The purification and recovery are carried out as in Example 1, except that recrystallisation was carried out from petroleum ether.

This yielded 0.547 g (39% yield) of trioctylphosphine oxide (TOPO) melting at 52° C.

EXAMPLE 20

The procedure of Example 1 was followed, but 5.5 mM of 3-chloropropionitrile were used. After 5 hours at 65° C., a dark oil was obtained. The product was distilled at 170° C. under 2.10$^{-5}$ mm Hg and under nitrogen. The final yield is 74% of dioctylpropionitrilephosphine oxide melting at 44°–45° C. and possessing, in the infra-red, a C≡N band at 2,215 cm$^{-1}$ and a P=O band at 1,140 cm$^{-1}$, but no P—H band. In the NMR, a triplet is observed at 2.74 ppm, corresponding to the methylene adjacent to the C≡N.

The elementary analysis is as follows:

|  | C | H | O | N | P |
|---|---|---|---|---|---|
| % calculated | 69.73 | 11.62 | 4.89 | 4.28 | 9.47 |
| % found | 69.45 | 11.59 | 4.89 | 4.22 | 9.20 |

EXAMPLE 21

The procedure of Example 1 was followed, using allyl bromide. After stirring for 4 hours at 65° C., the organic phase was treated as in Example 1 and a crude yield of 99% was obtained. The crude product was recrystallised from a mixture of acetone/water and the yield is then 73% of a product melting at 63°–65° C.

The product was finally recrystallised a further two times from petroleum ether and the final yield is 61% (0.702 g of product).

The product obtained, namely dioctylallylphosphine oxide, is a new product. It melts at 73.5°–74° C.

Its infra-red spectrum possesses a CH=CH band at 1,628 cm$^{-1}$ and a P=O band at 1,150 cm$^{-1}$.

Its NMR spectrum comprises: 1 multiplet 1H (=CH—) at 5.97 ppm; 1 triplet 2H (—CH$_2$=) at 5.30 ppm; 1 triplet 2H (—CH$_2$—) at 4.54 ppm; 1 multiplet 34H (2C$_8$H$_{17}$) between 0.88 and 1.65 ppm.

The product, which has the formula

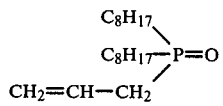

is hygroscopic.

EXAMPLE 22

The procedure of Example 1 was applied to 1.46 mM of 1,4-dichlorobut-2-ene, 3.65 mM of DOPO, 5 ml of 50% strength aqueous sodium hydroxide solution, 0.146 mM of TBAH and 10 ml of toluene.

After 6 hours at 65° C., the organic phase was separated off and treated as in Example 1. The excess DOPO was removed by washing twice with acetone at −20° C., after which the product was dissolved in cyclohexane and then recovered by cooling (precipitated).

This yielded a mixture consisting of 91% of the new compound of the formula:

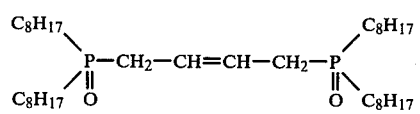

characterised by its infra-red spectrum:
CH=CH band at 1,650 cm$^{-1}$
P=O band at 1,140 cm$^{-1}$,
and 9% of the new compound of the formula:

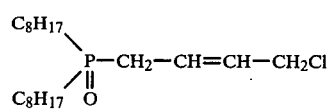

The total yield is 37%.

EXAMPLE 23

The procedure of Example 1 was followed, using 2.83 mM of di-(p-chloromethylphenyl) ether, 7.07 mM of DOPO, 10 ml of 50% strength aqueous sodium hydroxide solution, 0.283 mM of TBAH and 30 ml of toluene.

After stirring for 6 hours at 65° C., the mixture is treated as in Example 1 and 1.325 g of a mixture of new products are recovered (total yield: 69%), namely: 75% of

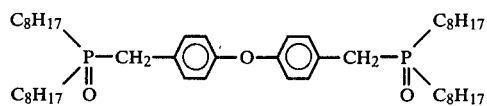

and 25% of

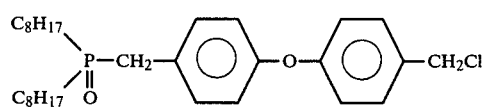

The mixture is characterised by its IR spectrum:

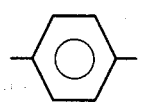

bands at 1,600 and 1,495 cm$^{-1}$

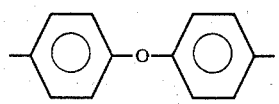

band at 1,230 cm$^{-1}$
P=O band at 1,150 cm$^{-1}$
no P—H band.

EXAMPLE 24

The procedure of Example 1 was followed, using 7.2 mM of DOPO, 30 ml of toluene, 2.9 mM of 1,4-di-(chloromethyl)-benzene, 5 ml of 50% strength aqueous sodium hydroxide solution and 0.29 mM of TBAH.

After stirring for 4 hours at 65° C., the compound of the formula:

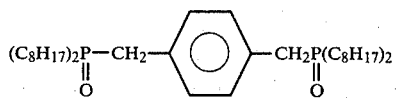

was obtained with a yield of 98%.

This new compound melts at 86°–88° C. and was identified by its infra-red spectrum (P=O band at 1,160 cm$^{-1}$ and C$_6$H$_4$ band at 1,505 cm$^{-1}$), its NMR spectrum (4H doublet of C$_6$H$_4$ at 7.24 ppm, 4H doublet of 2CH$_2$ at 3.08 ppm and 68H multiplet of 4C$_8$H$_{17}$ between 0.86 and 1.55 ppm) and its elementary analysis:

| C$_{40}$H$_{76}$O$_2$P$_2$ | C | H | O | P |
|---|---|---|---|---|
| % calculated | 73.85 | 11.69 | 4.92 | 9.53 |
| % found | 73.9 | 11.7 | 4.5 | 9.6 |

EXAMPLE 25

A random copolymer of styrene and p-chloromethylstyrene, containing 1.9 (x=1.9) units

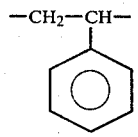

per 1.0 (y=1.0) unit

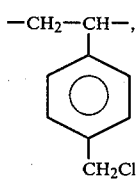

was used as the halogenomethyl derivative. The ratio x:y was thus 1.9:1 and the molecular weight of the copolymer was 170,000.

1.76 mM of DOPO and 0.07 mM of TBAH were added to a two-phase mixture of 50 ml of a toluene solution of the said polymer, containing 1.4 mM of chlorine, and 4 ml of 50% strength aqueous sodium hydroxide solution.

The mixture was stirred for 3 hours at 65° C. The polymer obtained was recovered, after precipitation in methanol, and purified by two successive cycles involving dissolution in chloroform and reprecipitation with methanol.

The polymer thus obtained was dried under a high vacuum and then analysed. The polymer comprised 1.9 groups

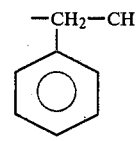

per group

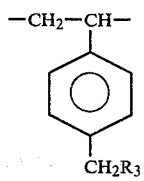

43% of the latter being of the type in which R$_3$=Cl and 57% being of the type in which R$_3$=PO(C$_8$H$_{17}$)$_2$.

The degree of substitution was thus equal to 57%. This analysis was carried out by infra-red, in which the CH$_2$Cl band is situated at 1,265 cm$^{-1}$ and the P=O band at 1,165 cm$^{-1}$, and by elementary analysis.

The molecular weight of the substituted polymer was 235,000 by osmometry, compared with a theoretical value of 236,000. From this, it is deduced that the process according to the invention does not degrade the chains.

EXAMPLE 26

The experiment of the preceding example was repeated, the 0.07 mM of TBAH being replaced by 0.07 mM of 222 and the toluene being replaced by benzene. The reaction temperature was lowered to 60° C. but the duration was extended to 16 hours. This yielded a polymer having an undegraded structure which was analogous to that of the polymer of Example 25, but in which the degree of substitution reaches 77% (determined by infra-red and elementary analysis).

EXAMPLE 27

The experiment of Example 25 was repeated using a resin in which x=2.05 and y=1.0, but a more vigorous stirring system was used. The polymer obtained possessed a degree of substitution of 86% and its molecular weight, measured by osmometry, was 300,000.

EXAMPLE 28

A Merrifield resin crosslinked with 2% of divinylbenzene and comprising 6.8 (x=6.8) groups

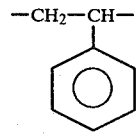

and 16.2 (y=16.2) groups

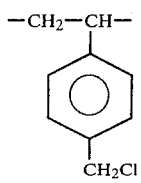

per group

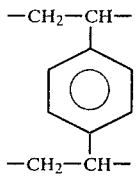

(z=1.0) was used as the halogenomethyl derivative.

This resin had a porosity of between 200 and 400 mesh.

The reaction was carried out as in Example 25, at 60° C. for 4 hours, with 1.277 g of Merrifield resin, 7.81 mM of DOPO, 1.25 mM of TBAH and 6 ml of 50% strength sodium hydroxide solution, and in 35 ml of toluene. Moreover, the resin had been swollen beforehand for 24 hours in toluene. The substituted resin obtained possessed the same structure as initially, but 5% of the groups

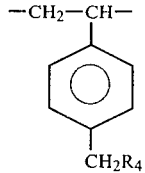

were of the type in which $R_4=Cl$ and 95% were of the type in which

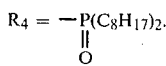

EXAMPLE 29

It was desired to show that it was possible for the organic medium in the process according to the invention not to contain solvent. The reaction was therefore carried out in bulk by vigorously stirring, for 3 hours at 65° C., 34.77 mM of benzyl chloride, 3.65 mM of DOPO, 0.11 mM of TBAH and 4 ml of 50% strength sodium hydroxide solution. The organic phase was treated as in Example 1. This yielded 1.44 g of crude product, this being a quantitative yield.

The infra-red spectrum of this product corresponded to dioctylbenzylphosphine oxide:
bands at 1,600 and 1,490 cm$^{-1}$ (phenyl)
band at 1,170 cm$^{-1}$ (P=O)
no PH band at about 2,300 cm$^{-1}$.

We claim:

1. Process for the synthesis of tertiary phosphine oxides from a secondary phosphine oxide and a halogenomethyl derivative, in the presence of a base, wherein a secondary phosphine oxide is reacted with a halogenomethyl derivative in an organic medium immiscible with water, in the presence of an aqueous phase containing an inorganic base and in the presence of a phase transfer catalyst and whilst stirring.

2. Process according to claim 1, wherein the secondary phosphine oxide has the general formula:

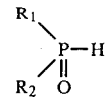

in which $R_1$ and $R_2$ are identical or different and are a linear or branched alkyl containing from 1 to 18 carbon atoms, or phenyl.

3. Process according to claim 1, wherein the halogenomethyl derivative has the general formula $XCH_2R$, in which: (a) X is a chlorine or bromine atom and R is a group $-CH=CHY$, in which Y is a hydrogen atom, a phenyl group or a group $-CH_2X$, in which X has one of the meanings indicated above, (b) R is

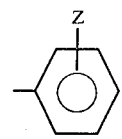

in which Z is hydrogen, $C_1$ to $C_4$ alkyl, vinyl, halogen, $-CH_2X$ or

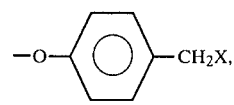

X having one of the meanings indicated above, (c) R is an alkyl chain containing from 1 to 12 carbon atoms, which is unsubstituted or substituted by at least one nitrile or epoxy, (d) R is phenyl forming part of a random copolymer chain containing styrene and a p-halogenomethylstyrene, which has a molecular weight of between 500 and 1,000,000 and comprises x and y units

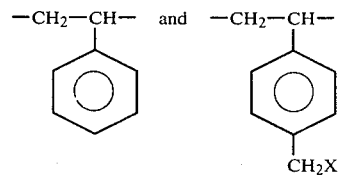

respectively, x and y being integers such that the ratio x:y is between 100:1 and 0:1, (e) R is phenyl forming part of a random copolymer chain containing styrene and a halogenomethylstyrene, which is partially crosslinked, has a molecular weight of between 1,000 and 1,000,000 and comprises x, y and z units

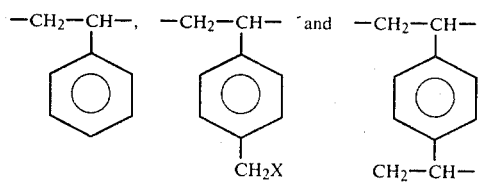

respectively, x, y and z being integers such that the ratio x:y is between 100:1 and 0:1 and such that the ratio z:y is between 1:25 and 1:5.

4. Process according to claim 1, wherein the aqueous phase containing an inorganic base is an aqueous solution containing from 30 to 60% by weight of sodium hydroxide or potassium hydroxide.

5. Process according to claim 1, wherein the phase transfer catalyst is a member selected from the group consisting of the quaternary ammonium, phosphonium or arsonium salts of the general formula:

in which Y=N, P or As, $A_1$, $A_2$, $A_3$ and $A_4$ are identical or different and are $C_1$ to $C_8$ alkyl, benzyl or polymer chains, and $X^-$ is an anion.

6. Process according to claim 1, wherein the phase transfer catalyst is a member selected from the group consisting of polyethylene oxides, crown ethers and cryptands.

7. Process according to claim 1, wherein the reaction is carried out at between 40° and 70° C.

8. Process according to claim 1, wherein the ratio of the volume of aqueous phase to the volume of organic phase is between 5:1 and 1:10.

9. Process according to claim 1, wherein the concentration of the reactants in the organic phase is between 0.1 and 20%.

10. Process according to claim 1, wherein the proportion of phase transfer catalyst, relative to the halogenomethyl derivative, is between 1 and 10 mol %.

11. The process, according to claim 1, wherein said organic medium is a solvent with a dielectric constant less than 8° at 20° C.

12. A tertiary phosphine oxide of formula:

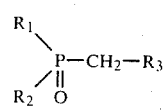

in which $R_1$ and $R_2$ are identical or different and are a linear or branched alkyl group containing from 1 to 18 carbon atoms, or phenyl and $R_3$ is a member selected from the group consisting of (a) a phenyl group forming part of one of the units

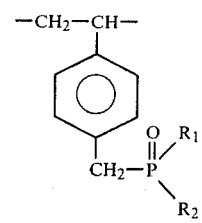

of a random copolymer derived from a random copolymer styrene and a p-halogenomethylstyrene, which has a molecular weight of between 550 and 1,100,000 and comprises x and y units

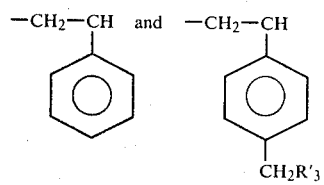

respectively, x and y being integers such that the ratio x:y is between 100:1 and 0:1, 20 to 90% by number of the $R_3$ groups being a group

and 10 to 80% being a chlorine or bromine atom, and (b) a phenyl forming part of one of the units

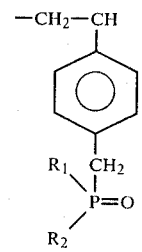

of a random copolymer derived from a random copolymer of styrene and a p-halogenomethylstyrene, which is partially crosslinked, has a molecular weight of between 1,100 and 1,100,000 and comprises x, y and z units

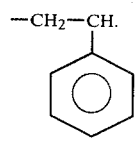

* * * * *
* * * * *